United States Patent [19]

Nathoo et al.

[11] Patent Number: 5,171,564
[45] Date of Patent: Dec. 15, 1992

[54] AQUEOUS TOOTH WHITENING DENTIFRICE

[75] Inventors: Salim A. Nathoo; Mary B. Chmielewski, both of Piscataway; Sahar Fakhry-Smith, Bordentown, all of N.J.

[73] Assignee: Colgate-Palmolive, New York, N.Y.

[21] Appl. No.: 759,241

[22] Filed: Sep. 13, 1991

[51] Int. Cl.$^5$ .................... A61K 7/16; A61K 7/20; A61K 33/40
[52] U.S. Cl. .................... 424/53; 424/613; 424/614; 424/615; 424/616; 424/54; 424/57
[58] Field of Search .................... 424/53, 613-616

[56] References Cited

U.S. PATENT DOCUMENTS

| | | | |
|---|---|---|---|
| 3,577,521 | 5/1971 | Scheller et al. | 424/57 |
| 4,223,003 | 9/1980 | Scheller | 424/53 |
| 4,350,681 | 9/1982 | Fulton | 424/53 |
| 4,405,599 | 9/1983 | Smigel | 424/53 |
| 4,592,487 | 6/1986 | Simon et al. | 424/53 |
| 4,603,045 | 7/1986 | Smigel | 424/53 |
| 4,812,308 | 3/1989 | Winston et al. | 424/53 |
| 4,837,008 | 6/1989 | Rudy et al. | 424/53 |
| 4,867,988 | 9/1989 | Chernock | 424/53 |
| 4,891,211 | 1/1990 | Winston | 424/53 |
| 4,897,258 | 1/1990 | Rudy et al. | 424/53 |
| 4,971,782 | 11/1990 | Rudy et al. | 424/53 |
| 4,976,955 | 12/1990 | Libin | 424/53 |
| 5,041,280 | 8/1991 | Smigel | 424/153 |

*Primary Examiner*—Shep K. Rose
*Attorney, Agent, or Firm*—Paul Shapiro; Robert C. Sullivan

[57] ABSTRACT

An aqueous abrasive oral composition which exhibits heightened and rapid whitening of teeth is obtained when using a combination of a dicalcium phosphate compound, a metal ion free peroxide, a chelating agent and a thickening agent.

15 Claims, No Drawings

AQUEOUS TOOTH WHITENING DENTIFRICE

BACKGROUND OF THE INVENTION

1. Field of the Invention

This invention relates generally to preparations for whitening human teeth, and more particularly, to a stable, storable composition which when applied onto the surface of teeth acts to whiten and polish teeth without damage to oral tissues.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth.

Dentifrices, especially toothpaste, gels and powders containing active oxygen or hydrogen peroxide liberating ingredients such as peroxides, percarbonates and perborates of alkali and alkaline earth metals or complex compounds containing hydrogen peroxide with salts of the alkali or alkaline earth metals have been disclosed in the prior art for the whitening of teeth. However, of all the peroxide compounds suggested by the prior art for whitening teeth, only two peroxide releasing compounds, urea peroxide and hydrogen peroxide, are approved by the Food and Drug Administration for use in oral compositions.

One method for whitening teeth used by dental professionals involves the use of 37% hydrogen peroxide in combination with heat and light to promote the oxidation reaction. This method, although fast, is losing favor with dentists because clinical and scientific evidence shows that high concentrations of peroxide are deleterious to oral tissues.

Another professional method for bleaching teeth involves the use of hydrogen peroxide generating compounds such as urea peroxide (carbamide peroxide) at concentrations of 10-20% to achieve the desired whitening effect. Urea peroxide rapidly breaks down into hydrogen peroxide due to the water present in saliva. This method known as an office-monitored at-home bleaching system involves the use of a mouth guard or tray within which the bleaching agent is placed. The tray is then placed upon the teeth of the patient and bleaching is allowed to take place. This method of treatment has drawbacks including tooth sensitivity, possibly due to demineralization and irritation of oral tissues. An additional disadvantage of the tray application method is that the bleaching effect is very slow.

There is a demand in the marketplace for a tooth whitening product that can be used at home or in private by the consumer and is safe and easy to use. A product for home use cannot utilize the compositions or products for whitening teeth that are available for use by a trained dental professional. For example, the 35% hydrogen peroxide bleaching agent utilized by many dental practitioners to bleach teeth is sufficiently concentrated to be irritating and potentially dangerous for home use by the consumer.

There are available in the marketplace non-abrasive dentifrice compositions for home use which contain 1-3% by weight concentrations of hydrogen peroxide and when brushed on the teeth effect whitening and removal of stains.

A drawback to home use bleaching dentifrices containing oxygen liberating bleaching compounds is the tendency of these products to decompose within a relatively short period of time following manufacture with concomitant loss of all or a substantial amount of the available oxygen thereby limiting the efficacy of these products as teeth whitening compositions. Peroxy compounds such as hydrogen peroxide are notoriously unstable with respect to maintenance of peroxide level and have been found to be difficult to formulate into aqueous gels or pastes which will have an adequate shelf-life and yet will readily liberate oxygen when applied to the oral cavity. Therefore, the prior art, for example U.S. Pat. Nos. 4,988,450 and 3,657,413 in formulating oxygen liberating compositions for the whitening of teeth utilize anhydrous powders or water-free pastes or gels which must be protected against contamination and chemical interaction. A drawback to the use of such anhydrous products is that, due to the absence of water, application of the oral composition tends to desiccate oral tissues which leads to irritation and tissue damage.

Whitening products formulated with peroxy compounds normally do not contain abrasive polishing agents as such materials activate the rapid decomposition of the peroxy compounds whereby the oxygen whitening agent is prematurely released. The gas evolution is especially undesirable with a toothpaste or gel product as such gas evolution can cause swelling and/or bursting of tubes containing same. Capped tubes filled with dentifrice products containing peroxy compounds and silica abrasives have been known to explode within one day after filling. When alumina abrasives are substituted for silica, the filled product is pocketed with gas holes within days of filling.

A drawback to the use of whitening products which are formulated without abrasives is that, in addition to having a slow bleaching action, the products are not effective in stain removal. Thus the polishing agent incorporated in a dentifrice acts to debride and physically scrub the external surface of teeth. This scrubbing action removes filmy bacterial and plaque layers as well as some of the stains and discoloring pigments that are found on teeth that cause the undesired discoloration. These polishing agents also microabrade the tooth so as to polish the teeth to give the enamel a more lustrous appearance and a higher optical sheen. This microabrasion action enhances the scrubbed teeth's ability to reflect white light and thereby appear brighter.

Illustrative of non-abrasive oral compositions containing peroxide compounds include U.S. Pat. Nos. 4,980,152; 4,839,156; 4,522,805 and 4,567,036.

U.S. Pat. No. 4,980,152 discloses a non-abrasive aqueous oral gel composition comprising about 0.5 to about 10% by weight urea peroxide and 0.01 to 2% by weight of a fluoride providing compound. The composition further includes a thickening agent such as carboxy polymethylene, a non-ionic surfactant such as Pluronic F127, alkali soluble cellulose ethers as viscosity increasing agents, potassium phosphate as a buffering agent and glycerine as a carrier and flavoring and sweetening agents.

U.S. Pat. No. 4,839,156 discloses an aqueous dental gel containing 18-25% by weight of a polyoxyethylene polypropylene block copolymer gelling agent, hydrogen peroxide, 15-40% by weight of a polyethylene glycol humectant, flavor, sweetening agent and a nonionic surfactant as the essential ingredients.

U.S. Pat. Nos. 4,522,805 and 4,567,036 disclose a stable toothpaste to aid in controlling periodontal disease, containing an oxidizing agent such as urea peroxide which dissociates into urea and hydrogen peroxide in the oral cavity, in a paste carrier comprising an anionic detergent, sorbitol and glycerin humectant and a thickening agent such as gum tragacanth, sodium alginate or sodium carboxymethyl cellulose.

U.S. Pat. No. 4,405,599 discloses a toothpaste consisting essentially of a combination of calcium peroxide and sodium perborate oxidizing agents, dicalcium phosphate, calcium carbonate and magnesium carbonate cleaning agents, sorbitol humectant, cornstarch, cellulose gum thickening agents, and an anionic detergent. There is no indication of the effect of the toothpaste on whitening or stain removal from teeth.

SUMMARY OF THE INVENTION

In accordance with the present invention, an aqueous abrasive oral composition which exhibits heightened and rapid whitening of teeth is obtained when using a combination of a dicalcium phosphate compound, a metal ion free peroxide, a chelating agent and a thickening agent as hereinafter defined.

As will hereinafter be illustrated, the oral compositions of the present invention in the form of an aqueous paste or gel is a stable, storable product which exhibits better whitening effect than previously attained by prior compositions, and the gels and pastes formed can be used for both office monitored at-home applications as well as in-home brushing applications.

DESCRIPTION OF THE PREFERRED EMBODIMENTS

The dentifrice compositions of the present invention are formulated using as the essential ingredients, a metal ion free peroxide compound as the whitening agent, a dicalcium phosphate compound as the abrasive polishing agent chelating agents such as sodium ethylene diamine tetracetic acid and sodium acid pyrophosphate, a thickening agent such as a poly (ethylene oxide) resin and a polyoxyethylene polyoxypropylene block copolymer thickener.

Examples of suitable metal ion free peroxide compounds used to prepare the oral compositions of the present invention include hydrogen peroxide and organic peroxides including urea peroxide, glyceryl peroxide, benzoyl peroxide and the like. A preferred organic peroxide is urea peroxide.

Typically, the peroxide compound can be employed in the composition of the present invention in amounts so that at least about 5% by weight of the composition comprises a peroxide. Preferably, the peroxide compound comprises from about 5 to about 20% by weight of the composition. More preferably, the peroxide comprises from about 10 to about 15% by weight of the composition. A typical peroxide concentration in the composition is generally about 10% by weight.

The term "dicalcium phosphate compound" as used herein includes within its meaning both dicalcium phosphate-dihydrate and anhydrous dicalcium phosphate or calcium pyrophosphate. Dicalcium phosphate-dihydrate and calcium pyrophosphate are compounds which have long been used as cleaning agents in toothpastes. These calcium phosphate compounds have remineralizing properties, their ionic constituents are practically the same as those contained in dental enamel, which they combine with the property of imparting excellent cleaning and polishing effects to oral compositions made therefrom.

In preparing the aqueous abrasive oral compositions of the present invention, the dicalcium phosphate compound is included in the compositions of the present invention in an amount of from about 25 to about 60% by weight, preferably from about 30 to about 55%.

Glycerin, sorbitol and polyethylene glycol in combination with water are useful as carrier materials in the composition of the present invention. A combination of polyethylene glycol and water are preferred as the carrier.

Illustrative of the polyethylene glycols useful in the practice of the present invention include polyethylene glycols known by the trademark CARBOWAX which are nonionic polymers of ethylene oxide having the general formula:

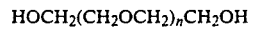

$$HOCH_2(CH_2OCH_2)_nCH_2OH$$

wherein n represents the average number of oxyethylene groups. The Carbowax polyethylene glycols are designated by a number such as 400, 600, 800, etc. which represents the average molecular weight. The average molecular weight of the polyethylene glycols used herein is about 200–1000, preferably 400–800 and most preferably 600 (PEG 600).

The glycerine, sorbitol or polyethylene glycol is included in the compositions of the present invention in an amount of from about 2 to about 20% by weight and preferably about 5 to about 15% by weight. Water is incorporated in the aqueous dentifrice compositions of the present invention at a concentration of about 5 to about 30% by weight of the composition and preferably about 15 to about 25% by weight.

Surfactants are also included in the dentifrice compositions of the present invention and serve as solubilizing, dispersing and emulsifying agents. The surfactant constitutes about 0.05 to 3.0% by weight and preferably 0.1 to 1% by weight of the oral composition.

Particularly useful surfactants include nonionic surfactants such as a water soluble polyoxyethylene monoester of sorbitol with a $C_{10-18}$ fatty acid ester of sorbitol (and sorbitol anhydrides), consisting predominantly of the monoester, condensed with about 10–30, preferably about 20, moles of ethyleneoxide. The fatty acid (aliphatic hydrocarbon-monocarboxylic acid) may be saturated or unsaturated, e.g. lauric, palmitic, stearic, oleic acids. Tween 20, which is a polyoxyethylene (20) sorbitan monolaurate is especially preferred as a surfactant in compositions containing hydrogen peroxide.

Other useful surfactants include anionic surfactants such as water soluble salts of higher fatty acid monoglyceride monosulfates, such as sodium salts of the monosulfated monoglycerides, or hydrogenated coconut oil fatty acids, higher alkylsulfates, such as sodium lauryl sulfate and alkyl aryl sulfonates, such as sodium dodecyl benzene sulfonate. Sodium lauryl sulfate is especially preferred as a surfactant in compositions containing urea proxide.

The flavor ingredient constitutes about 0.5-5.0% by weight of the dentifrice composition of the present invention. Suitable flavoring constituents are flavoring oils, e.g., oils of spearmint, peppermint, methyl salicylate, sassafras, clove, sage, eucalyptus, marjoram, cinnamon, and menthol.

A sweetening material is preferably also employed as a complement to the flavoring material. Suitable sweetening agents are water soluble and include sodium saccharin, sodium cyclamate, xylitol, aspartame and the like, in concentrations of about 0.01 to 1.0% by weight. Sodium saccharin is preferred.

Thickening or gelling agents used in the formulation of the dentifrice include nonionic polyoxyethylene polyoxypropylene block copolymers and poly (ethylene oxide) resins. Illustrative of polyoxyethylene polyoxypropylene block copolymers useful in the practice of the present invention include block copolymers having the formula

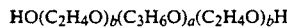

$HO(C_2H_4O)_b(C_3H_6O)_a(C_2H_4O)_bH$ wherein a is an integer such that the hydrophobic base represented by $(C_3H_6O)$ has a molecular weight of about 2750 to 4000, b is an integer such that the hydrophilic portion (moiety) represented by $(C_2H_4O)$ constitutes about 70-80% by weight of the copolymer. Block copolymers of this composition are available commercially under the trademark Pluronic F type.

Pluronic F127, which has a molecular weight of 4000 and contains 70% of the hydrophilic polyoxyethylene moiety is preferred in the practice of the present invention. Poly (ethylene oxide) resinous thickeners are available commercially in a molecular weight range of 50,000 to 5,000,000.

Polyox N-10 available from Union Carbide Corp. as granules of water soluble poly (ethylene oxide) pseudoplastic resin having a molecular weight of about 100,000 and a Brookfield viscosity of 44 CPS (25° C., spindle 1, speed 50 rpm) is a preferred poly(ethylene oxide) pseudoplastic resin thickener for use in the dentifrice compositions of the present invention.

Other pseudoplastic resins such as acrylic acid polymers and cellulose esters may also be used as thickeners in the whitening compositions of the present invention.

The thickening agents are preferably present in the dentifrice in an amount within the range of about 1.0 to about 20 percent by weight and about 3 to about 10 percent by weight is preferred for use in the dentifrice compositions of the present invention.

Agents which chelate metal ions are an essential ingredient of the present invention. Suitable chelating agents include sodium acid pyrophosphate, disodium calcium ethylene diamine tetraacetic acid ($Na_2Ca$ EDTA), phosphoric acid, citric acid, sodium citrate, potassium citrate, sodium pyrophosphate, potassium pyrophosphate, disodium, ethylenediamine tetraacetate and other amino polycarboxylic acids. The chelating agents are incorporated in the dentrifice compositions of the present invention in an amount within the range of 0.1 to about 8.0% by weight and preferably about 0.5 to about 3.0% by weight.

Fluorine-providing salts having anti-caries efficacy may also be incorporated in the dentifrice of the present invention and are characterized by their ability to release fluoride ions in water. Among these materials are inorganic metal salts, for example, sodium fluoride, potassium fluoride, cuprous fluoride, a tin fluoride such as stannous fluoride or stannous chlorofluoride, sodium fluorosilicate, ammonium fluorosilicate, sodium monofluorophosphate, alumina mono-and di-fluorophosphate.

It is preferable to employ a fluoride compound to release about 10–1500 ppm of fluoride ion.

In addition, anti-foaming agents such as simethicone may also be incorporated in the dentifrice compositions of the present invention at a concentration of 0.001 to about 0.1% by weight of the composition.

The aqueous, abrasive dentifrice composition of the present invention may be prepared by suitably mixing the ingredients under vacuum. The resulting paste is then tubed.

The following examples are further illustrative of the present invention, but it is understood that the invention is not limited thereto. All amounts and proportions referred to herein and in the appended claims are by weight unless otherwise indicated.

EXAMPLE I

An aqueous, abrasive whitening paste was prepared using the following ingredients:

| INGREDIENTS | % |
|---|---|
| Urea Peroxide | 10.0 |
| Calcium Pyrophosphate | 27.5 |
| Di Calcium phosphate dihydrate | 5.0 |
| Glycerine | 5.045 |
| PEG-600 | 10.0 |
| Polyox N-10 | 5.0 |
| Sodium lauryl Sulfate | 0.2 |
| $Na_2C_a$ EDTA | 1.0 |
| Simethicone | 0.005 |
| $Na_2H_2P_2O_7$ | 2.0 |
| Methyl Salicylate | 0.75 |
| DI $H_2O$ | 18.4 |
| Pluronic F-127 | 15.0 |
| Saccharin | 0.1 |

The paste was prepared in a Ross mixer. Water, sodium acid pyrophosphate and Polyox N-10 were stirred for 30 minutes. Pluronic F-127 and Polyethylene Glycol 600 were added and the mixture stirred for 1.5 hours at a vacuum of −15 mmHg. Urea Peroxide was added to the mixture and stirring was continued for an additional 30 minutes at −15 mmHg vacuum. Simethicone, saccharin, Na₂CaEDTA, sodium lauryl sulfate and flavor were added and mixed for 15 minutes without vacuum. Then, a vacuum of 30 mmHg was applied and stirring continued for an additional 30 minutes. Calcium Pyrophosphate was added and stirring was continued for 30 minutes under vacuum (−30 mmHg). Dicalcium phosphate dihydrate and glycerine were added and mixed for a further 30 minutes under vacuum. The resulting product was a paste. The product when packaged in a tube was stable and could be stored without evidence of peroxide decomposition.

To determine the whitening efficacy of the paste, three caries-free natural stained human molars were pumiced with Mytol (trademark) Tooth Cleaning Paste, and the initial color was determined by reflectance spectrometry using the Minolta Chroma Meter. The teeth were immersed in the paste prepared in Example I and periodically removed and examined over a 4 hour period, and five readings of L, a and b were taken of each examined tooth.

The change in color was then calculated using the equation:

$$\text{delta E} = [(\text{delta L*})^2 + (\text{delta a})^2 + (\text{delta b*})^2]^{\frac{1}{2}}$$

Where delta E represents an increase in whiteness. The higher the delta E value, the whiter the tooth, a delta E value of 14 being the most white and a delta E value of 1 being the least white or discolored. These values are based on the calibration of the Minolta chroma meter using the Trubyte Bioform (trademark) color ordered shade guide.

The delta E values are recorded in Table I below.

For purposes of comparison, the procedure of Example I was repeated with the exception that comparative Composition C which did not contain calcium pyrophosphate, or the chelating agents dicalcium sodium EDTA, phosphoric acid, and sodium acid pyrophosphate was also tested for whiteness. The results obtained with this comparative composition designated composition "C" are also recorded in Table I below.

When the composition of Example I was prepared without the chelating agents and the product tubed, bubbles rapidly formed in the product with the eventual bursting of the tube.

For purposes of further comparison, the procedure of Example I was repeated with the exception that a professional tooth bleaching gel obtained from a dentist consisting of urea peroxide in an anhydrous glycerine base was also tested for whitening. The results obtained with this commercial product designated Composition "$C_1$" are also recorded in Table I.

TABLE I

| Composition | Increase in Whiteness Delta E HOURS | | |
|---|---|---|---|
| | 1 | 2 | 4 |
| EX. 1 | 5.5 | 6.4 | 8.1 |
| C | 2.4 | 3.4 | 4.7 |
| $C_1$ | 2.11 | 3.5 | 4.78 |

The delta E values recorded in Table I show the increased whiteness of human molars obtained with an oral composition of the present invention, especially when compared with the comparative compositions C and $C_1$.

EXAMPLE II

An aqueous, abrasive paste was prepared using the following ingredients:

| INGREDIENTS | % |
|---|---|
| $H_2O_2$ (35%) | 10.0 |
| Dicalcium phosphate di-hydrate | 50.0 |
| PEG-600 | 7.5 |
| Phosphoric Acid | 0.5 |
| $Na_2CaEDTA$ | 1.0 |
| Methyl salicylate | 0.75 |
| Tween 20 | 0.60 |
| DI $H_2O$ | 19.55 |
| Pluronic F-127 | 10.0 |

| INGREDIENTS | % |
|---|---|
| Saccharin | 0.1 |

The ingredients were mixed together in a Ross mixer. In preparing the paste composition, a gel was first made by mixing water, Polyethylene Glycol 600 and Pluronic F-127 for 1 hour under vacuum and then allowed to stand under vacuum for at least 1 hour. After a clear gel was formed, the 35% hydrogen peroxide solution and phosphoric acid were added to the resulting mixture and stirring was continued for another 1 hour period under vacuum. Sodium saccharin, disodium-calcium EDTA, Tween-20 and methyl salicylate were then added and the stirring was continued under vacuum for an additional 1 hour. Finally, dicalcium phosphate dihydrate was added and the mixture stirred under vacuum for 2 hours, and left overnight under vacuum. The resulting product was a paste.

The tooth whitening efficacy of the paste of Example II was tested using a Minolta Chroma Meter following the procedure of Example I. The results are recorded in Table II.

For purposes of comparison, Composition $C_1$ was again tested for whitening efficacy. The results of this comparative test are also recorded in Table II.

When the composition of Example II was prepared without the chelating agents, phosphoric acid and $Na_2C_a$ EDTA, and the product tubed, bubbles rapidly formed in the product with the eventual bursting of the tube.

TABLE II

| Composition | Increase in Whiteness Delta E Hours | | |
|---|---|---|---|
| | 1 | 2 | 4 |
| EX. II | 2.36 | 4.44 | 6.25 |
| $C_1$ | 2.11 | 3.50 | 4.78 |

The delta E values recorded in Table II show the increased whiteness of human molars obtained with the composition of the present invention, especially when compared with the comparative composition $C_1$.

We claim:

1. An aqueous abrasive oral composition which exhibits heightened and rapid whitening of teeth, the composition being comprised of about 15 to about 25% by weight water, about 25 to about 60% by weight of a dicalcium phosphate abrasive, about 5 to about 30% by weight of a metal ion free peroxide, about 0.1 to about 8.0% by weight of a chelating agent and about 1.0 to about 20% by weight of a thickening agent.

2. The composition of claim 1 wherein the dicalcium phosphate compound is calcium pyrophosphate.

3. The composition of claim 1 wherein the dicalcium phosphate compound is dicalcium phosphate dihydrate.

4. The composition of claim 1 wherein the metal ion free peroxide is hydrogen peroxide.

5. The composition of claim 1 wherein the metal ion free peroxide is urea peroxide.

6. The composition of claim 1 wherein the chelating agent is disodium calcium ethylene diamine tetracetic acid.

7. The composition of claim 1 wherein the chelating agent is phosphoric acid.

8. The composition of claim 1 wherein the chelating agent is $Na_2H_2P_2O_7$.

9. The composition of claim 1 wherein the chelating agent is a combination of disodium calcium ethylene diamine tetracetic acid, phosphoric acid and $Na_2H_2P_2O_7$.

10. The composition of claim 1 wherein the thickener is a polyoxyethylene polyoxypropylene block copolymer.

11. The composition of claim 1 wherein the thickener is a poly (ethylene oxide) resin.

12. The oral composition of claim 1 wherein the dicalcium phosphate compound is incorporated in the composition at a concentration of about 25 to about 60% by weight.

13. The composition of claim 1 wherein the chelating agent is incorporated in the composition at a concentration of about 0.1 to about 5.0% by weight.

14. The composition of claim 1 wherein the metal ion free peroxide is incorporated in the composition at a concentration of about 5.0 to about 20% by weight.

15. The composition of claim 1 wherein the thickener is incorporated in the composition at a concentration of about 1.0 to about 20% by weight.

* * * * *